(12) United States Patent
Horn (10) Patent No.: US 7,865,229 B2
(45) Date of Patent: *Jan. 4, 2011

(54) SYSTEM AND METHOD FOR DETERMINING PATH LENGTHS THROUGH A BODY LUMEN

(75) Inventor: Eli Horn, Kiryat Motzkin (IL)

(73) Assignee: Given Imaging, Ltd., Yoqneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/536,841

(22) Filed: Aug. 6, 2009

(65) Prior Publication Data
US 2009/0292182 A1    Nov. 26, 2009

(51) Int. Cl.
*A61B 1/00*    (2006.01)

(52) U.S. Cl. .................. 600/424; 600/117; 600/476

(58) Field of Classification Search .................. 600/424, 600/117; 128/899
See application file for complete search history.

(56) References Cited

U.S. PATENT DOCUMENTS

| | | | |
|---|---|---|---|
| 3,460,528 A | 8/1969 | Carney | |
| 3,683,890 A | 8/1972 | Beal | |
| 3,971,362 A | 7/1976 | Pope et al. | |
| 4,178,735 A | 12/1979 | Jackson | |
| 4,239,040 A | 12/1980 | Hosoya et al. | |
| 4,262,632 A | 4/1981 | Hanton et al. | |
| 4,278,077 A | 7/1981 | Mizumoto | |
| 4,439,197 A | 3/1984 | Honda et al. | |
| 4,507,115 A | 3/1985 | Kambara et al. | |
| 4,646,724 A | 3/1987 | Sato et al. | |
| 4,689,621 A | 8/1987 | Kleinberg | |
| 4,803,992 A | 2/1989 | Lemelson | |
| 4,819,620 A | 4/1989 | Okutsu | |
| 4,844,076 A | 7/1989 | Lesho et al. | |
| 4,936,823 A | 6/1990 | Colvin et al. | |
| 4,940,997 A | 7/1990 | Hamlin et al. | |
| 5,042,486 A | 8/1991 | Pfeiler et al. | |
| 5,081,041 A | 1/1992 | Yafuso et al. | |
| 5,109,870 A | 5/1992 | Silny et al. | |

(Continued)

FOREIGN PATENT DOCUMENTS

DE    2929429    2/1980

(Continued)

OTHER PUBLICATIONS

Office Action European Application No. 05 755 436.2-1265 dated Dec. 2, 2009.

(Continued)

*Primary Examiner*—Eric F Winakur
*Assistant Examiner*—Helene Bor
(74) *Attorney, Agent, or Firm*—Pearl Cohen Zedek Latzer, LLP (57) ABSTRACT

A system and method for determining the path length through a body lumen, for example to a specified location, is described. A location detection system may identify the location in space of an in-vivo device over time. A path-length detection unit may use data from the location detection system to determine a path traveled by an in-vivo device. A site of interest along that path may be identified. The distance of the site of interest from at least one end point of a body lumen may be determined.

18 Claims, 3 Drawing Sheets

U.S. PATENT DOCUMENTS

| | | |
|---|---|---|
| 5,187,572 A | 2/1993 | Nakamura et al. |
| 5,211,165 A | 5/1993 | Dumoulin et al. |
| 5,267,033 A | 11/1993 | Hoshino |
| 5,279,607 A | 1/1994 | Schentag et al. |
| 5,330,427 A | 7/1994 | Weissenburger |
| 5,368,027 A | 11/1994 | Lubbers et al. |
| 5,377,678 A | 1/1995 | Dumoulin et al. |
| 5,395,366 A | 3/1995 | D'Andrea et al. |
| 5,398,670 A | 3/1995 | Ortiz et al. |
| 5,429,132 A | 7/1995 | Guy et al. |
| 5,479,935 A | 1/1996 | Essen-Moller |
| 5,495,114 A | 2/1996 | Adair |
| 5,549,109 A | 8/1996 | Samson et al. |
| 5,558,640 A | 9/1996 | Pfeiler et al. |
| 5,604,531 A | 2/1997 | Iddan et al. |
| 5,671,739 A | 9/1997 | Darrow et al. |
| 5,697,384 A | 12/1997 | Miyawaki et al. |
| 5,730,129 A | 3/1998 | Darrow et al. |
| 5,782,765 A | 7/1998 | Jonkman |
| 5,800,350 A | 9/1998 | Coppleson et al. |
| 5,819,736 A | 10/1998 | Avny et al. |
| 5,837,196 A | 11/1998 | Pinkel et al. |
| 5,913,820 A | 6/1999 | Bladen et al. |
| 5,929,901 A | 7/1999 | Adair et al. |
| 5,936,406 A | 8/1999 | Potthast |
| 5,946,813 A | 9/1999 | Nachbaur et al. |
| 5,986,693 A | 11/1999 | Adair et al. |
| 5,993,378 A | 11/1999 | Lemelson |
| 6,043,839 A | 3/2000 | Adair et al. |
| 6,082,366 A | 7/2000 | Andra et al. |
| 6,099,482 A | 8/2000 | Brune et al. |
| 6,149,581 A | 11/2000 | Klingenstein |
| 6,174,291 B1 | 1/2001 | McMahon et al. |
| 6,228,048 B1 | 5/2001 | Robbins |
| 6,230,038 B1 | 5/2001 | Von Gutfeld et al. |
| 6,233,476 B1 | 5/2001 | Stormmer et al. |
| 6,240,312 B1 | 5/2001 | Alfano et al. |
| 6,285,897 B1 | 9/2001 | Kilcoyne et al. |
| 6,304,766 B1 | 10/2001 | Colvin, Jr. |
| 6,324,418 B1 | 11/2001 | Crowley et al. |
| 6,330,464 B1 | 12/2001 | Colvin et al. |
| 6,369,812 B1 | 4/2002 | Lyrilboz et al. |
| 6,385,482 B1 | 5/2002 | Boksberger et al. |
| 6,395,562 B1 | 5/2002 | Hammock et al. |
| 6,428,469 B1 | 8/2002 | Iddan et al. |
| 6,473,635 B1 | 10/2002 | Rasche |
| 6,475,145 B1 | 11/2002 | Baylor |
| 6,488,694 B1 | 12/2002 | Lau et al. |
| 6,618,612 B1 | 9/2003 | Acker et al. |
| 6,632,175 B1 | 10/2003 | Marshall |
| 6,692,430 B2 | 2/2004 | Adler |
| 6,709,387 B1 | 3/2004 | Glukhovsky et al. |
| 6,741,882 B2 | 5/2004 | Schaffer et al. |
| 6,757,557 B1 | 6/2004 | Bladen et al. |
| 6,804,547 B2 | 10/2004 | Pelzer et al. |
| 6,813,512 B2 | 11/2004 | Aldefeld et al. |
| 6,871,086 B2 | 3/2005 | Nevo et al. |
| 6,904,308 B2 | 6/2005 | Frisch et al. |
| 6,923,768 B2 | 8/2005 | Camus et al. |
| 6,944,316 B2 | 9/2005 | Glukhovsky et al. |
| 6,947,787 B2 | 9/2005 | Webler |
| 6,950,690 B1 | 9/2005 | Meron et al. |
| 6,992,477 B2 | 1/2006 | Govari |
| 6,996,432 B2 | 2/2006 | Ostrovsky et al. |
| 7,010,338 B2 | 3/2006 | Ritter et al. |
| 7,076,284 B2 | 7/2006 | Segawa et al. |
| 2001/0017649 A1 | 8/2001 | Yaron |
| 2001/0025135 A1 | 9/2001 | Naito et al. |
| 2001/0035902 A1 | 11/2001 | Iddan et al. |
| 2002/0015952 A1 | 2/2002 | Anderson et al. |
| 2002/0042562 A1 | 4/2002 | Meron et al. |
| 2002/0099310 A1 | 7/2002 | Kimchy et al. |
| 2002/0103417 A1 | 8/2002 | Gazdzinski |
| 2002/0109774 A1 | 8/2002 | Meron et al. |
| 2002/0146368 A1 | 10/2002 | Meron et al. |
| 2002/0158976 A1 | 10/2002 | Vni et al. |
| 2002/0173718 A1 | 11/2002 | Frisch et al. |
| 2002/0177779 A1 | 11/2002 | Adler et al. |
| 2002/0198470 A1 | 12/2002 | Imran et al. |
| 2003/0018280 A1 | 1/2003 | Lewkowicz et al. |
| 2003/0020810 A1 | 1/2003 | Takizawa et al. |
| 2003/0023150 A1 | 1/2003 | Yokoi et al. |
| 2003/0028078 A1 | 2/2003 | Glukhovsky |
| 2003/0045790 A1 | 3/2003 | Lewkowicz et al. |
| 2003/0114742 A1 | 6/2003 | Lewkowicz et al. |
| 2003/0167000 A1 | 9/2003 | Mullick et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0195415 A1 | 10/2003 | Iddan |
| 2003/0208107 A1 | 11/2003 | Refael |
| 2003/0214579 A1 | 11/2003 | Iddan |
| 2003/0214580 A1 | 11/2003 | Iddan |
| 2003/0216622 A1 | 11/2003 | Meron et al. |
| 2004/0027459 A1 | 2/2004 | Segawa et al. |
| 2005/0065441 A1 | 3/2005 | Glukhovsky |

FOREIGN PATENT DOCUMENTS

| | | |
|---|---|---|
| DE | 34 40 177 | 6/1986 |
| FR | 2 688 997 | 10/1993 |
| IL | 126727 | 10/1998 |
| IL | 143258 | 5/2001 |
| IL | 143259 | 5/2001 |
| JP | 4144533 | 5/1992 |
| JP | 6114037 | 4/1994 |
| JP | 6285044 | 10/1994 |
| JP | 7111985 | 5/1995 |
| JP | 7289504 | 11/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001231744 | 8/2001 |
| JP | 2001245844 | 9/2001 |
| JP | 2002010990 | 1/2002 |
| JP | 2000342524 | 6/2002 |
| JP | 2000342525 | 6/2002 |
| WO | WO 99/32028 | 7/1999 |
| WO | WO 01/10291 | 2/2001 |
| WO | WO 01/50941 | 7/2001 |
| WO | WO 01/65995 | 9/2001 |
| WO | WO 01/69212 | 9/2001 |
| WO | WO 02/055126 | 7/2002 |
| WO | WO 02/055984 | 7/2002 |
| WO | WO 02/067593 | 8/2002 |
| WO | WO 02/094337 | 11/2002 |
| WO | WO 02/102223 | 12/2002 |
| WO | WO 03/003706 | 1/2003 |
| WO | WO 03/005877 | 1/2003 |
| WO | WO 03/011103 | 2/2003 |
| WO | WO 2004/028336 | 4/2004 |

| | | | |
|---|---|---|---|
| WO | WO 2004/035106 | 4/2004 | |

OTHER PUBLICATIONS

U.S. Appl. No. 09/807,892, filed Jun. 6, 2001, Meron et al.
U.S. Appl. No. 10/200,548, filed Jul. 23, 2002, Glukhovsky et al.
U.S. Appl. No. 10/724,109, filed Dec. 1, 2003, Glukhovsky et al.
U.S. Appl. No. 10/166,025, filed Jun. 11, 2002, Lewkowicz et al.
U.S. Appl. No. 10/213,345, filed Aug. 7, 2002, Glukhovsky.
U.S. Appl. No. 60/297,761, filed Jun. 14, 2001, Lewkowicz et al.
U.S. Appl. No. 60/299,178, filed Jun. 20, 2001, Glukhovsky et al.
U.S. Appl. No. 60/507,508, filed Oct. 2, 2003, Horn et al.
BBC News Online—Pill camera to 'broadcast from the gut', Feb. 21, 2000, www.news.bbc.co.uk, printed Oct. 22, 2002.
Evaluation of the heidelberg pH capsule: Method of Tubeless Gastric Analysis, Yarbrough, III et al., The American Journal of Surgery, vol. 117, Feb. 1969, pp. 185-192.
Heidelberger Kapsel—ein Kleinstsender für die pH-Messung im Magen, Lange, et al., Telefunken-Zeitung, Jg 36 (1963) Heft 5, pp. 265-270.
"In Pursuit of the Ultimate Lamp", Craford et al., Scientific American, Feb. 2001.
International Search Report for PCT/IL99/0554 dated Apr. 4 2000.
International Search Report of PCT/IL02/00391, dated May 19, 2003.
Katgraber F, Glenewinkel F, Fischler S, Int J. Legal Med 1998; 111(3) 154-6.
Manual of Photogrammetry, Thompson (Ed.), Third Edition, Volume Two, Copyright 1944, 1952, 1966 by the American Society of Photogrammetry.
"New Smart Plastic has Good Memory"—Turke, European Medical Device Manufacturer, devicelink.com, Sep. 2001.
PCT Search Report International Application No. PCT/IL02/00386 International Filing Date: May 19, 2002.
"Robots for the Future"—Shin-ichi, et al. http://jin.jcic.or.jp/nipponaia13/sp05 html.printed Nov. 29, 2001.
Rowell, Nancy D., Endoscopes Go Wireless, Biophotonics in Action, Photonics Spectra, pp. 60-62, Mar. 2001.
Supplementary Partial European Search Report, Mar. 19, 2004.
Video Camera to "TAKE"—RF System Lab, Dec. 25, 2001.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
"Wellesley Company Sends Body Montiors into Space"—Crum, Boston Business Journal, 1998.
www.jason.net/tinycam.htm, © 2001, printed Dec. 19, 2001.
www.middleeasthealthmag.com/article2.htm—Review proves the value of computers, © 2001, printed Nov. 29, 2001.
www.pedinc.com Personal electronic devices, © 1997.
www.rfnorkia.com—NORIKA3, printed on Jan. 1, 2002.
Office Action for U.S. Application No. 10/879,053 mailed on Apr. 4, 2008.
Office Action for U.S. Application No. 10/879,053 mailed on Oct. 16, 2008.
Office Action for U.S. Application No. 10/879,053 mailed on Dec. 1, 2006.

SYSTEM AND METHOD FOR DETERMINING PATH LENGTHS THROUGH A BODY LUMEN

FIELD OF THE INVENTION

The present invention relates to an in-vivo device traveling through a body lumen, and in particular to a system and method to determine the path length or distance through a body lumen to a specified location.

BACKGROUND OF TH INVENTION

The gastrointestinal (GI) tract may typically be a convoluted long tube that folds many times to fit inside the abdomen, proceeding through the esophagus, stomach, small intestine, and large intestine. Autonomous in-vivo devices, for example, ingestible devices that may move through the GI tact, and that may collect data and transmit the data to a receiver system, are known in the art. Such devices may be used to examine areas that may otherwise be difficult to access with non-autonomous devices such as for example, endoscopes, colonscopes, gastroscopes, enteroscopes, laparoscopes, catheters, etc.

During examination of a patient with an autonomous device, a physician may identify one or more sites of interest. A physician may want to revisit the sites of interest using, for example, an alternate device (e.g. endoscope, colonscope, a second autonomous device etc). Revisiting may be for more examining, sensing, diagnosing, treating, surgery, etc. In some instances, a physician may attempt to revisit a site of interest with a non-autonomous device only to discover that the site of interest is beyond the range that the non-autonomous device can penetrate. In other instances, an attempt to revisit the site of interest may be carried out with more than one alternate device before succeeding in locating the site of interest. This may lead to unnecessary discomfort, cost, and potential risk to the patient.

SUMMARY OF THE INVENTION

Various embodiments of the present invention provide a system and method for determining path length through a body lumen, for example path length or distance to a specified location. In some embodiments of the present invention a raw path length of the in-vivo device traveling to a specified location along a body lumen may be compared to a raw path length of the in-vivo device traveling through the entire body lumen. The ratio between the two path lengths together with a pre-selected body lumen length may be used to determine a true path length through a body lumen to a specified location. Typically the system of the present invention may include an in-vivo device, a location detection system and a path-length detection unit. Other configurations may be used.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the system, and method of the present invention may typically be used in conjunction with an in-vivo sensing device and system such as described in embodiments in U.S. Pat. No. 5,604,531 to Iddan et al. and/or in International Application number WO 01/65995 entitled "A Device And System For In-Vivo Imaging", published on 13 Sep. 2001, both of which are assigned to the common assignee of the present invention and both of which are hereby incorporated by reference. Other embodiments of the system and method of the present invention may be used in conjunction with an in-vivo device and system such as is described in embodiments in International Application number WO/03005877, entitled "Device and method for examining a body lumen", published on Jan. 23, 2003, which is assigned to the common assignee of the present invention and is hereby incorporated in its entirety by reference. Alternate embodiments of the system and method of the present invention may be used with other devices, e.g. non-imaging and/or non-in-vivo devices.

Embodiments of the in-vivo device that may be used together with the system and method of the present invention may typically be autonomous and may typically be self-contained. For example, the in-vivo device may be a capsule or another unit where all the components may be substantially contained within a container or shell, and where the in-vivo device may not require any wires or cables to, for example, receive power or transmit information. The in-vivo device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Embodiments of the present invention may typically include a location detection system for locating the device in vivo, for example, as is described in embodiments of US Patent Application Publication Number US 20020173718, published on Nov. 21, 2001 and entitled "Array System and Method for Locating an In Vivo Signal Source", which is hereby fully incorporated by reference. It is noted that in other embodiments of the invention, other location detecting methods may be used. For example, in one embodiment of the present of invention, location information may be determined by, for example, including one or more transmitting antennas in an in vivo device, to transmit data using various frequencies, and/or by detecting the location of the in vivo device using components of quasi-static magnetic field(s)—a magnetic method. In some embodiments, methods such as those using ultrasound transceivers or monitors that include, for example, three magnetic coils that receive and transmit positional signals relative to an external constant magnetic field may be used. In yet other embodiments, GPS-like system may be used; for example, a system using transmission from three or more stations. Typically, in some embodiments of the present invention, an array of antennas or sensors may be placed on or close to the abdomen to enable tracking of the in vivo device. Of course, other components or sets of components may be used in accordance with embodiments of the invention.

In one embodiment, a set of locations of the in-vivo device may be determined, and from these locations a distance or path length may be determined. The locations may be determined from the data that is sensed by the device—for example, a radio signal including image or other data may be analyzed for location.

Figure 1:
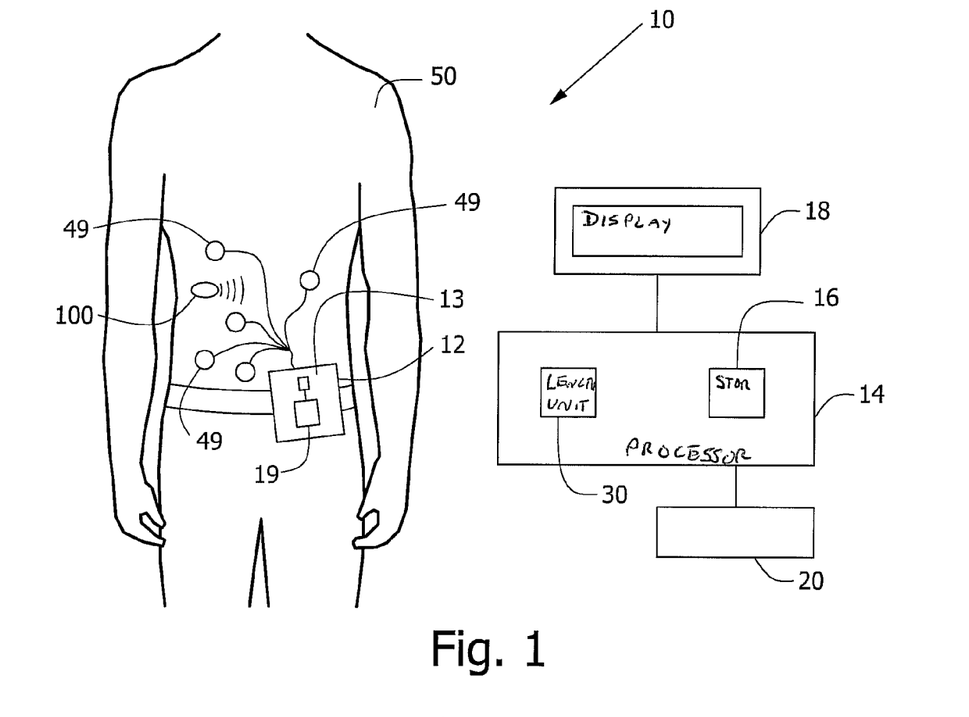
FIG. 1 is a schematic illustration of an in-vivo system according to an embodiment of the present invention.

Reference is now made to FIG. 1 showing an in-vivo system 10 according to an embodiment of the present invention. In-vivo system 10 may include an in-vivo device 100, an external recorder 12, a processing unit 14, a display unit 18, and a user input unit 20. In-vivo device 100 may be any suitable traceable or trackable in-vivo device. In some embodiments of the present invention, device 100 may typically be, for example, an in-vivo imaging device, for example as is described in embodiments in U.S. Pat. No. 5,604,531 and/or in International Application number WO 01/65995, that may transmit signals, for example, images through for example an RF channel. Transmitted signals may, for example, be picked-up by an array of antennas 49 that may be, for example, positioned and/or worn on a patient's body 50. Recorder 12 may typically be a portable wearable receiving and recording device and may include a signal pick up system, for example, antenna array 49.

Recorder 12 may, for example, receive signals from antennas 49 and store them, for example, temporarily in for example, a portable storage unit 19. Recorder 12 may include a location detection system 13 that may in one embodiment of the invention utilize, for example, a triangulation method to determine the location of in-vivo device 100 relative to the antenna array 49. The triangulation method may be based, for example, on the difference in signal strength picked up from the transmitting in-vivo device by the various antennas in antenna array 49. Typically, the location detection system 13 and method may be similar to that described in US Patent Application Publication Number US20020173718. Other suitable location detection systems may be used. In other embodiments of the present invention, location detection system 13 may be wholly or partially integral to data processor 14.

Location data obtained from the location detection system 13 as well as signals or data transmitted by in-vivo device 100 may be, in one embodiment of the invention, for example, downloaded to processor 14 for post-processing, and storage in, for example, storage unit 16. In other embodiments, device 100 may be or include another transmitting device other than an imaging device, for example, an in-vivo device with an RFID tag, or device 100 may be, for example, a non-transmitting in-vivo device, for example a marker, or other traceable, trackable or locatable devices.

A physician or other operator may, for example, use an in-vivo sensing system 10 to, for example, examine, diagnose, check for strictures, treat, and/or perform surgery on a patient. For example, an in-vivo sensing device 100 may, for example, capture images as it travels through the GI tract and transmit them to a recorder 12 external to the body. An external recorder 12 may store the transmitted images as well as other data, for example location data indicating the position in space of the transmitting device. In one embodiment, location data may be determined from sensed data. For example, sensed data such as image data or pressure data may be transmitted, and from the transmissions (e.g., via triangulation) location data may be determined. In other embodiments, the sensed data itself may be analyzed for location data, such as by determining from a set of images distance traveled between images.

After reviewing the transmitted data, for example the images and/or image stream, a physician may identify a site that may be of interest, for example, a location where an in vivo device captured an image(s) indicating, for example, a pathological area in the GI tract that may need further diagnosis, examination, or treatment. In some embodiments of the present invention, a site of interest may be other than a site where pathology may have been identified, a site of interest may be any specified location. In other embodiments, the in-vivo sensing device may include other sensors besides or in addition to image sensors, for example, temperature sensor, pH sensors, blood sensors, etc. and the specified location may be determined based on reviewing data other than image data. In other embodiments of the invention, the in vivo device may be other than a sensing device, or have other functions in addition to sensing, for example, medicine delivery, treatment, or biopsy.

Following examination and/or treatment with an in-vivo autonomous device, a physician may want to revisit one or more sites or location points of interest using an alternate device (e.g. endoscope, colonscope, gastroscope, enteroscope, laparoscope, and another autonomous in-vivo device, etc). It may be helpful for the physician to know how deep into the body lumen the device may need to be inserted in order to reach the location point of interest. This may aid in choosing a procedure, and/or equipment for revisiting. Pre-knowledge of the path length, may help the physician reach the location point of interest more quickly so as to shorten the procedure time (e.g. examination, diagnostic, or treatment) and in that reduce the patient's discomfort. In an alternate embodiment, this information may help a physician decide if it is at all possible to reach the location point of interest with alternate devices. For example, there may be some areas, for example, in the small intestine that may not be reachable with for example with an endoscope, or colonscope, etc. Surgical intervention may be necessary in some circumstances. In some embodiments of the present invention, prior knowledge of the path length to the site may help avoid unsuccessful attempts to approach a site that may not be possible to access. Path length information may be used for other applications. Further, path length other than to a specific or selected location may be obtained using embodiments of the present invention; for example, path length to arbitrary or multiple points, path length after certain times; times to certain path lengths, etc.

Location detection system, such as location detection system 13, may be useful for indicating the location of a transmitting device in space, the motility, as well as the speed at given period of time. However, for body lumens that may be convoluted, it may be difficult to deduce how far through a body lumen a device advanced to reach a location point of interest from knowledge of its instantaneous position in space. In addition, it may be difficult to use an instantaneous location in space to locate a site of interest at a later time, since some body lumens may not be stationary over time. An instantaneous location of a site of interest within a body lumen may change over time and thus it may be difficult to predict its location with respect to the shifting body lumen when revisiting the site.

Typically, processor 14 may also include or be associated with a path-length detection unit 30, to for example, to determine the path length through a body lumen, for example up to a specified location, or in another manner. Data obtained from the location detection system 13, as well as other data, may be used as input to path-length detection unit 30. Other data to be used as input to the path-length detection unit 30 may, for example, include user input data 20 or data from other features of system 10. Path-length detection unit 30 may in some embodiments include one or more software units within processor 14.

Path-length detection unit 30 may typically in some embodiments of the present invention, involve post-processing location data obtained from location detection system 13 and, for example, downloaded from recorder 12. In some embodiments of the present invention, the path-length detection unit 30 may be a stand-alone unit, may be integral to data processor 14 with storage unit 16, and/or integral to data recorder 12. The path-length detection unit 30 may typically include processing and storing capability. In some embodiments of the present invention, the path-length detection unit 30 may include input systems for a user, as well as display systems for displaying to the user, for example, display unit 18. Path-length detection unit 30 may, in other embodiments of the present invention, be partially or entirely integral to recorder 12, and may, for example, not receive user input. Processor 14 may typically be a personal computer but may be any suitable unit for processing and/or storing data. Signals, data, and location related data may for example, be displayed on display unit 18.

Figure 2:
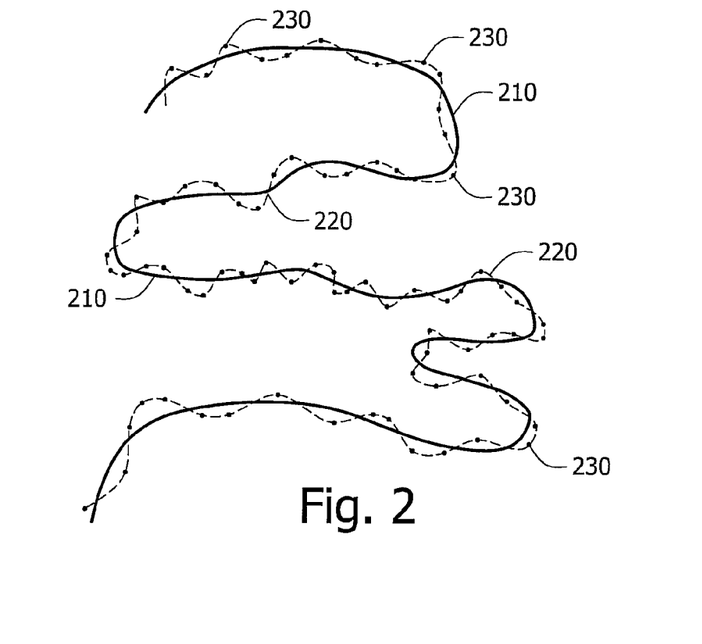
FIG. 2 is a schematic illustration of a simulated body lumen and a superimposed estimated path through measured location points according to an embodiment of the present invention.

Reference is now made to FIG. 2 showing a simulated body lumen path 210 (solid line) that an in-vivo device may be, for example, traveling in and a set of example location points 230, obtained from a location detection system 13 along the simulated path. An estimated path may be drawn by interpolating between consecutive points to obtain, for example, the estimated path 220 (dashed line). The raw path length may be determined, for example, by integrating the distances between consecutive points using known methods. Small errors may exist when estimating the location data. Errors may be due to, for example, random noise or from the device 100 shifting its orientation in-vivo. When estimating the raw path length through, for example, path 220, the small errors in estimating location may accumulate into large errors in estimating a length of a path especially for long paths such as for example, the path of the small intestine, or other paths in the GI tract, or other body lumens. Calculating the path traveled by an in-vivo device using, for example, the estimated path 220 may, for example, lead to a path much longer than the true path. Smoothing may be used to reduce the error however since the true path may in itself be torturous and unpredictable, it may be difficult to smooth the curve with good precision.

Typically, in some embodiments of the invention, it may be possible to assume that the noise level of the output signal from location detection system 13 may be substantially similar along the entire path through which the in-vivo device travels. As such, a relative path length ($L_R$) represented by the ratio between raw path length to a location point of interest (L) and the raw total path length though the entire body lumen ($L_T$) may be used to estimate more accurately the path length to a location point of interest without the need of separating, or otherwise eliminating the noise from the signal. In one embodiment, the ratio may be described by the following relationship:

$$L_R = L/L_T.$$

Other formulas may be used. In one embodiment, a set of calculated paths, such as a calculated total path length in a lumen and a calculated length to a specified point or target or targets, may be determined. The known or estimated total lumen length may be determined, and a ratio between the known or estimated length and the calculated total length may be determined. This ratio may be applied to the calculated path length of the device to the specified point or points, to determine a more accurate estimated path length or distance to the point or points.

When the in-vivo device may be closer to an existing end point of a body lumen it may be useful for a user to know the relative distance from the existing end point since that may be the direction through which the site may be revisited. As such the following relationship may be used:

$$L_R = L/L_T;\ L \leq L_T/2$$

$$L_R = (L_T - L)/L_T\ L > L_T/2$$

Other formulas may be used. For a clearer indication of the path length from an end point of a body lumen, a pre-selected overall length of the body lumen may be used. For example, the small intestine may be known to be on average 6 to 8 meters long. In one example, 7 meters may be used as a pre-selected value for the length of the small intestine. Using this estimation, the actual path length ($L_A$) may be expressed by the following equations:

$$L_A = 7*L/L_T;\ L \leq L_T/2$$

$$L_A = 7*(L_T - L)/L_T\ L > L_T/2$$

Other formulas may be used.

Figure 3:
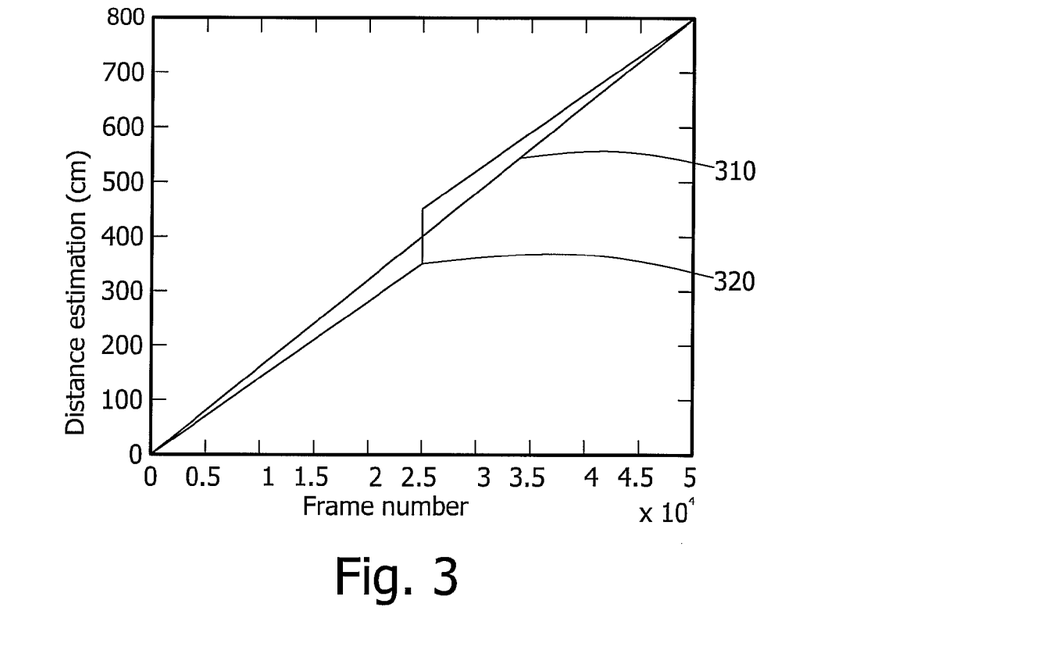
FIG. 3 is an estimated maximum error distribution resulting from using an estimated value of the total length of a body lumen, according to an embodiment of the present invention.

Reference is now made to FIG. 3 showing an estimated error distribution resulting from using a pre-selected value (as opposed to a true value) of the length of a body lumen, and assuming no error due to location detection (the location detection error is not taken into account in this figure), according to one embodiment of the present invention; other values and curves may be used. The horizontal axis may mark the number of frames, for an in-vivo device transmitting image frames to an external recorder 12 at, for example, a given frequency. The vertical axis may mark the path length traveled through a body lumen determined by location points calculated from transmission signals of each image frame. Curve 310 may represent the true distance traveled. Curve 320 may represent the estimated distance determined, for example, by the method described herein.

As may be seen by the curves in FIG. 3, the greatest discrepancy between the true path length (310) and estimated path length (320) through a body lumen may be near the middle of the body lumen path while the smallest discrepancy between the true (310) and estimated (320) path length through body lumen may be near each of the end points of the body lumen. In some embodiments of the present invention, it may be desirable to estimate the distance through the small intestine so that a site of interest may be revisited for example by an enteroscope and/or a colonoscope. Enteroscopes, for example, may only be able to penetrate, for example, approximately a half a meter beyond the top entrance to the small intestine, for example, the pylorus. Colonoscopes, for example, may only be able to penetrate, for example, a few centimeters beyond the cecum and into the small intestine. As such accuracy near the end points may be of greater importance than accuracy for example half way along the small intestine.

Figure 4:
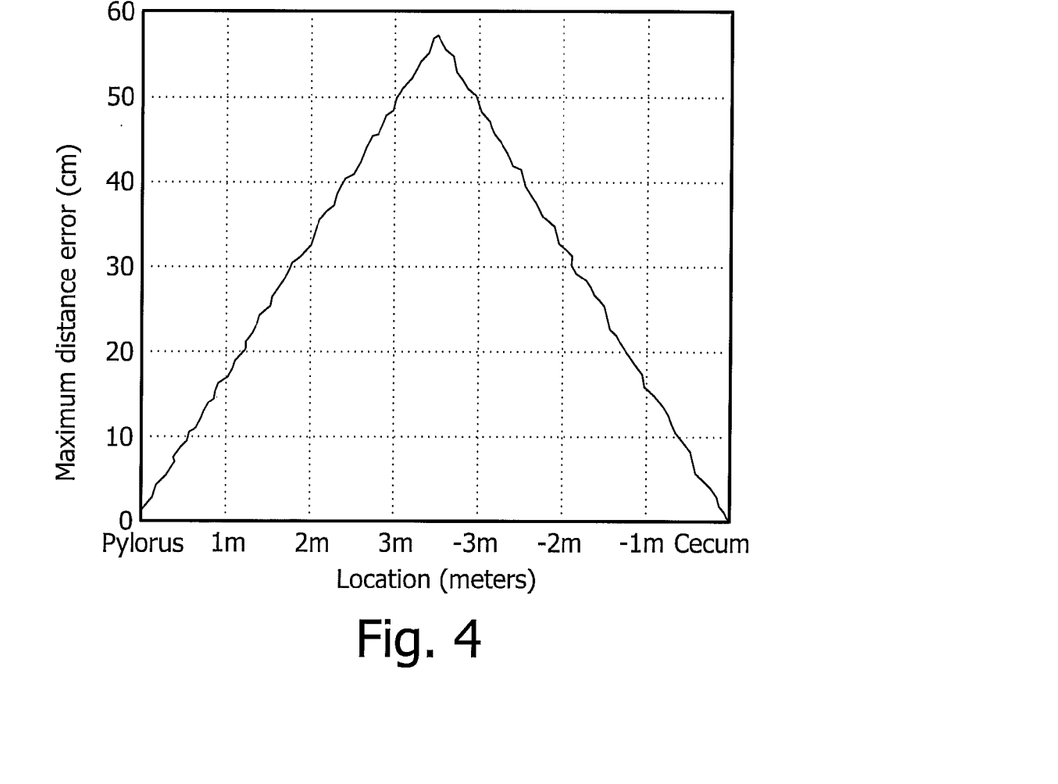
FIG. 4 is a simulated maximum distance error as a function of location along a small intestine according to an embodiment of the present invention.

Reference is now made to FIG. 4 showing an exemplary simulated maximum distance error as a function of distance along a small intestine, according to one embodiment of the present invention; other functions may be used, and other lumens may be examined. In this exemplary simulation, the pylorus may be marked as the entrance of the small intestine and the cecum may be marked as the point of exist of the small intestine. The location detection error in this graph may be modeled, for example, as a Rayleigh distribution with, for example, the average distance error of 3.5 cm that may, in some embodiments of the invention, be a typical location detection error. In other embodiments of the present invention, other models and error levels may be used. In this exemplary model, as may be seen by the graph in FIG. 4, the error of the path length through the body lumen may be in the order of magnitude of 10 cm at a distance of 0.5 meter from an end point (entrance and/or exist) of the small intestine marked by the cecum and pylorus respectively. As such, a physician may have indication if a site detected by an autonomous in-vivo device may be revisited by an alternate device and from which direction.

When an in-vivo device may travel through more than one lumen or portion of lumen in its course, for example, esophagus, stomach, and small intestine, it may be useful to be able to locate the end point of the lumen of interest, for example, the small intestine and measure the path length from that end point of that lumen. Various methods may be used for this purpose. For example, pH measurement may be used to detect a change in pH when entering and/or exiting the stomach. A pressure sensor may be used to indicate when device 100 was released from, for example, the small intestine into the roomier large intestine. In one embodiment of the present invention, a pressure indicator may be used to detect, for example, the rhythmic peristaltic pressure that may be typical in the small intestine. In some embodiments of the present invention, other methods involving post-processing of images may be used to identify mucosa and/or tissue that may, for example, be typically found in a specific body lumen. In other embodiments, for example, a specific color scheme that may typically be found in a specific body lumen may be used to identify the end points through a body lumen. In yet other embodiments, a physician or medical technician may identify through image or other data, the end points of a body lumen and use, for example, user input unit 20 to input that information to path-length detection unit 30.

Figure 5:
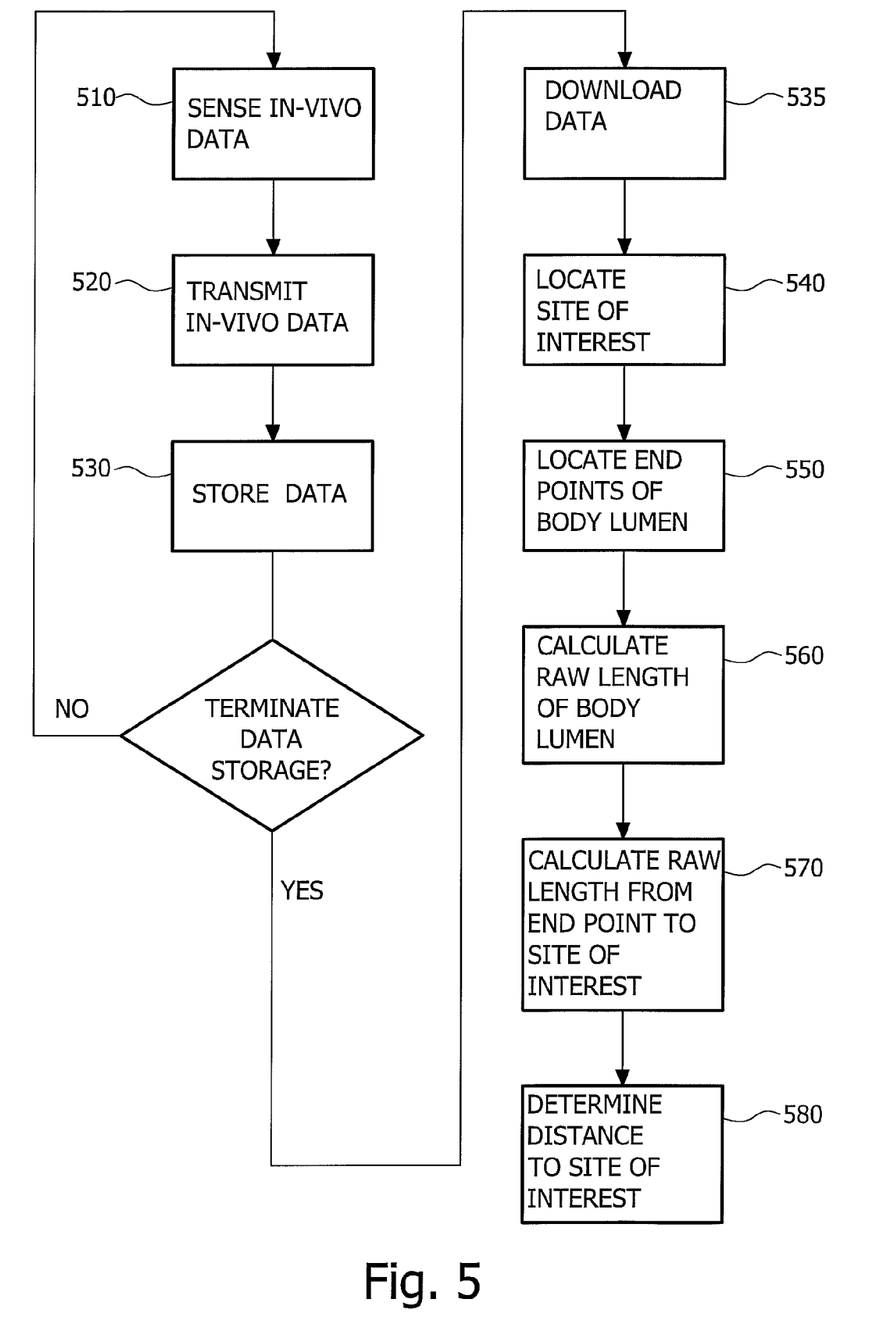
FIG. 5 is a flow chart describing a method for determining distance through a body lumen according to some embodiment of the present invention.

Reference is now made to FIG. 5 showing a flow chart describing a method for determining a path length through a body lumen up to a specified location, according to one embodiment of the present invention. In block 510 an in-vivo device may sense data or a condition from within a body lumen. In some embodiments of the invention, the sensed data may be image data, for example, image data captured within the body lumen of the GI tract. Other data may be sensed instead of or in addition to image data, for example, temperature, pressure, motility, etc.

Data captured or collected may be, for example, transmitted (block 520). In other embodiments pure location data (e.g., via a carrier signal or other signal) may be transmitted; further, transmission need not occur. For example, externally generated signals (e.g., X-rays, ultrasound signals) may be used to determine location data. In other embodiments of the present invention, a signal other than the data sensed may be transmitted to indicate a specified condition was met, for example, a signal to indicate that an in-vivo device may be caught behind a stricture, or other conditions. The data transmitted may be picked up by one or more pick up devices, for example one or more antennas 49. The transmitted data and the data pertaining to the location of the in-vivo device (obtained by location detection system 13) may be, for example, stored in recorder 12 (block 530). Typically, the process of sensing (block 510), transmitting (block 520), and storing (block 530) may continue for predetermined time period until all relevant data may be assumed to have been collected and stored. Other methods of determining a suitable time for termination of data collection and storage may be used.

In block 535, sensed data and location data may be downloaded to, for example, data processor 14. According to some embodiments no downloading may be required. In other embodiments of the present invention, transmitted data may be directed (by wire or wireless connection) to processing unit 14 in real time. A user may review data transmitted from an in-vivo device, for example, a stream of images. When reviewing the data, the user may mark one or more images that may be of interest, for example, may show pathology. The image or images of interest may be marked with any suitable user input means 20, for example, keyboard, computer mouse, touch-sensitive screen, and/or other suitable means. Data from the location detection system may be used to determine the location of a site of interest, for example a site where the marked images were captured in-vivo (block 540). In one embodiment of the present invention, a user may mark, for example, images that indicate the entrance and exit points of the body lumen containing the image of interest. In other embodiments, marking need not be used, and path length data may be generated independent of specific or requested points.

Data from the location detection system may be used to determine the location of the end points of the body lumen (block 550). In other embodiments of the present invention, the end points of the body lumen may be located without user input, for example, by methods described herein. In other embodiments of the present invention, the end points may be recognized by for example, a change of color, visible texture, measured pH, measured pressure, etc. In other embodiments of the present invention, the end points may be recognized by using a tissue color bar as may be described in embodiments described in U.S. provisional application 60/507,508, entitled, "Device, System And Method For Presentation Of In-Vivo Data," which is hereby incorporated by reference in its entirety. Other methods of determining end points of body lumens may be implemented.

In block 560 the data pertaining to the location of the in-vivo device may be processed to determine the raw path length through the body lumen from the entrance to the exit point ($L_T$). In block 570 the raw path length from the determined entrance point of the body lumen to the location point of interest (L) may be calculated. In block 580 the actual path length ($L_A$) may be determined based on raw path lengths $L_T$ and L, and a pre-selected length of the overall length of the body lumen. In other embodiments of the present invention, the actual path length ($L_A$) may be based on other suitable input data besides or in addition to the input data described herein. For example, path lengths $L_T$ and L may be preprocessed before calculating their ratio for determining the actual path length. Typically, the path-length detection unit 30 may perform tasks described in blocks 560 through blocks 580. In other embodiments of the present invention, the tasks described in blocks 560 to 580 may be shared by more than one unit or component in system 10, for example the tasks may be shared by location detection system 13. A health professional may use the information obtained on the path length to, to help him decide how to proceed with diagnosis or treatment of a patient.

Other steps and series of steps may be used.

While the invention has been described with respect to a limited number of embodiments, it will be appreciated that many variations, modifications and other applications of the invention may be made. Embodiments of the present invention may include other apparatuses for performing the operations herein. Such apparatuses may integrate the elements discussed, or may comprise alternative components to carry out the same purpose. It will be appreciated by persons skilled in the art that the appended claims are intended to cover all such modifications and changes as fall within the true spirit of the invention.

The invention claimed is:

1. A computer-implemented method for determining a path length from an end point of a body lumen to a site of interest in the body lumen, the method comprising the steps:

obtaining location data of a wireless in vivo device;

determining, using a processing unit, a raw path length value of the in vivo device between an end point of the body lumen and the site of interest, based upon the location data of the in vivo device;

determining a raw total lumen length value based upon the location data of the in vivo device;

calculating, using the processing unit, a relative path length value using a ratio between the raw path length value and the raw total lumen length value;

calculating, using the processing unit, an actual path length between the end point of the body lumen and the site of interest, using the relative path length value and a pre-selected overall lumen length value; and displaying the actual path length value.

2. The method according to claim 1 wherein the end point of the body lumen is an entrance point or an exit point of the body lumen.

3. The method according to claim 2 wherein an end point of the body lumen is selected from the group consisting of: pylorus and cecum.

4. The method according to claim 1 wherein the actual path length equals the product of the pre-selected overall lumen length value and the relative path length value.

5. The method according to claim 1 comprising selecting the end point which is closer to the location of the site of interest.

6. The method according to claim 1 wherein the body lumen is the small intestine, and wherein the pre-selected overall lumen length value is between 6 and 8 meters.

7. The method according to claim 1 further comprising determining the location of the end point of the body lumen based on data sensed by the in vivo device.

8. The method according to claim 1 comprising obtaining the location data of the in vivo device based on triangulation of signal strength received by antennas of an external receiving system.

9. The method according to claim 1 further comprising:

post-processing images sent from the in vivo device to identify end points of said body lumen; and providing indication to the user if the site of interest may be revisited by an alternate device.

10. The method according to claim 9 further comprising providing indication to the user from which direction the site of interest may be revisited by the alternative device.

11. A computer-implemented method for determining a path length from an end point of a body lumen to a site of interest in the body lumen, the method comprising the steps:

obtaining location data of an autonomous in vivo device;

determining, using a processing unit, a raw path length value of the in vivo device between an end point of the body lumen and the site of interest, based upon the location data of the in vivo device;

determining a raw total lumen length value based upon the location data of the in vivo device;

calculating, using the processing unit, a ratio between a pre-selected overall lumen length value and the raw total lumen length value;

calculating, using the processing unit, an actual path length between the end point of the body lumen and the site of interest, by multiplying the raw path length value by said ratio; and displaying the actual path length value and an identification of said end point of the body lumen.

12. The method according to claim 11 wherein the end point of the body lumen is an entrance point or an exit point of the body lumen.

13. The method according to claim 12 wherein an end point of the body lumen is selected from the group consisting of: pylorus and cecum.

14. The method according to claim 12 comprising selecting the end point which is closer to the location of the site of interest, in order to determine a shorter raw path length value.

15. The method according to claim 11 wherein the body lumen is the small intestine, and wherein the pre-selected overall lumen length value is between 6 and 8 meters.

16. The method according to claim 11 further comprising determining the location of the end point of the body lumen based on image data.

17. The method according to claim 11 further comprising determining the location of the end point of the body lumen based on data sensed by the in vivo device.

18. The method according to claim 11 comprising obtaining the location data of the in vivo device based on triangulation of signal strength received by antennas of an external receiving system.

* * * * *